US006592510B1

(12) United States Patent
Plentev

(10) Patent No.: US 6,592,510 B1
(45) Date of Patent: Jul. 15, 2003

(54) DEVICE FOR PROPHYLAXIS AND TREATMENT OF DISEASES OF LUMBAR, COXOFEMORAL AND PELVIC ORGANS OF A HUMAN BODY

(76) Inventor: Sergey Vladimirovich Plentev, 54-32, Soltysa Street, 220070 Minsk (BY)

( * ) Notice: Subject to any disclaimer, the term of this patent is extended or adjusted under 35 U.S.C. 154(b) by 261 days.

(21) Appl. No.: 09/605,976

(22) Filed: Jun. 28, 2000

(51) Int. Cl.$^7$ .................................................. A61N 1/00

(52) U.S. Cl. ............................ 600/14; 600/594; 601/15

(58) Field of Search ................................ 600/9, 10, 11, 600/12, 13, 14, 15, 594; 601/15, 18, 19, 24, 25, 26, 46–60, 89–102

(56) References Cited

U.S. PATENT DOCUMENTS

| | | | | |
|---|---|---|---|---|
| 5,140,977 A | * | 8/1992 | Raffel | 601/46 |
| 5,197,940 A | * | 3/1993 | Sievert et al. | 600/9 |
| 5,312,315 A | | 5/1994 | Mortensen et al. | 482/113 |
| 5,314,400 A | * | 5/1994 | Tsby et al. | 600/9 |
| 5,378,215 A | | 1/1995 | Kreitenberg | 482/57 |
| 5,397,285 A | | 3/1995 | Chang | 482/62 |
| 5,397,286 A | | 3/1995 | Haan et al. | 482/61 |
| 5,429,585 A | * | 7/1995 | Liang | 601/15 |

FOREIGN PATENT DOCUMENTS

| | | | | |
|---|---|---|---|---|
| CN | 1058707 A | * | 2/1992 | A47C/1/025 |
| DE | G9300499 | | 4/1993 | |
| GB | 0 209 246 A1 | * | 1/1987 | A61N/1/42 |
| WO | WO9427678 | | 12/1994 | |

OTHER PUBLICATIONS

Physiotherapy Manual under editor V.G. Jasnogorodski M. Medicinia 1992 p. 13.

Methodical Reference Book, NIINNF of Ministry Health of Republic of Belarus, Minsk 1990 p. 14.

2d International Conf. “Theoretical and Clinical Aspects of Bio–resonance and Multiresonance Therapy.” Imrdiz, Moscow 1996 pp. 21–30.

* cited by examiner

*Primary Examiner*—Kevin Shaver
*Assistant Examiner*—Pamela Wingood

(57) ABSTRACT

The present invention relates to the field of medicine and in particular to prophylaxis and therapy of diseases of pelvic and coxofemoral organs of a human body.

Figure 1:
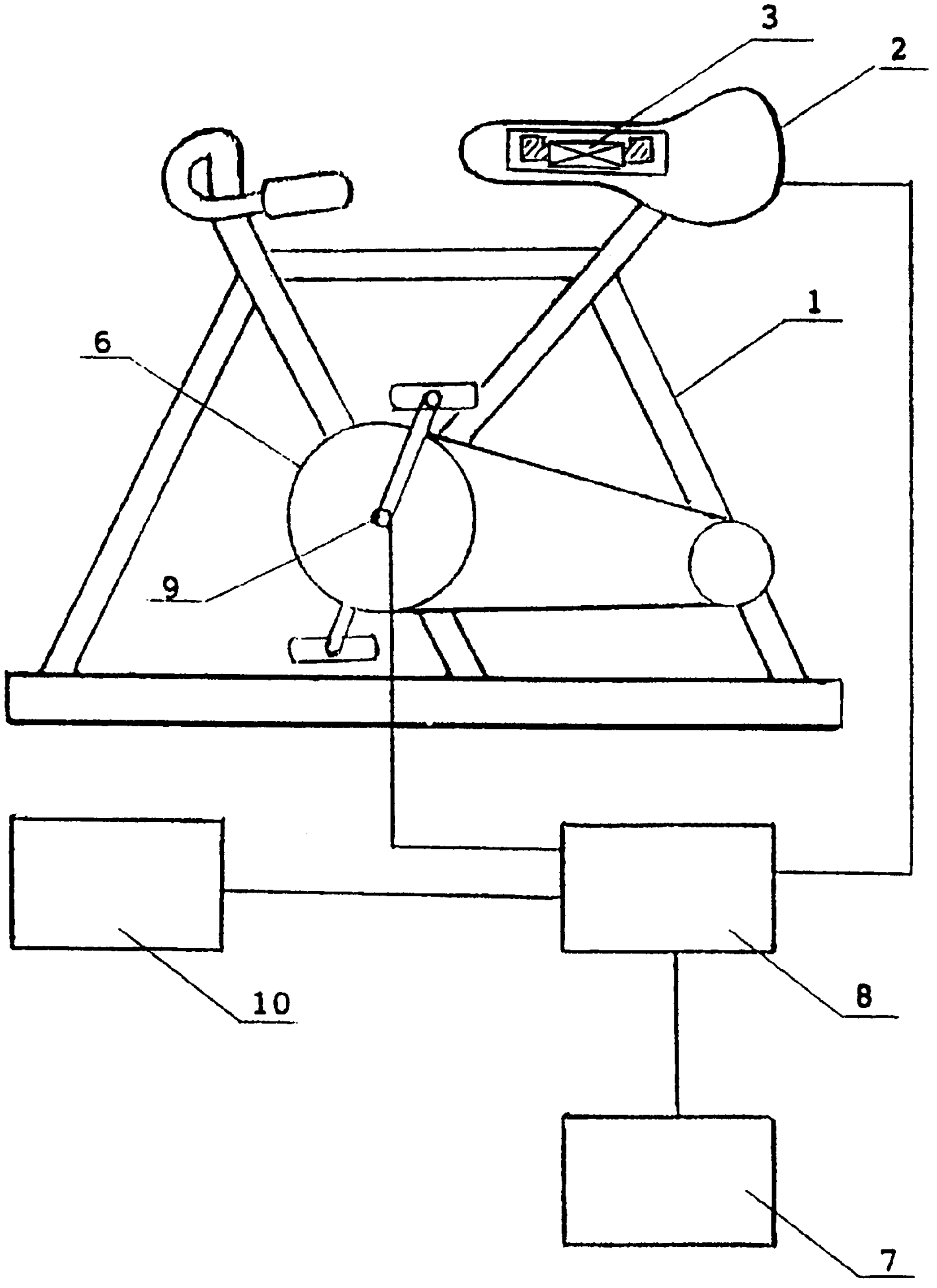

The prophylactic and therapeutic effect is produced by combination of a physical work of human locomotor system subjecting of internal organs to modulated magnetic field. Magnetic field is modulated by signals supplied from the detector of motion or/and from the output of the audiosystem for listening-in music.

3 Claims, 2 Drawing Sheets

DEVICE FOR PROPHYLAXIS AND TREATMENT OF DISEASES OF LUMBAR, COXOFEMORAL AND PELVIC ORGANS OF A HUMAN BODY

The present invention relates to the field of medicine and in particular to prophylaxis and therapy of diseases of pelvic and coxofemoral organs of a human body.

The prior art discloses devices for training muscles of locomotor system of a human body, rehabilitation after various diseases, prophylaxis of diseases. The devices comprise a supporting frame with a seat and dynamic elements for physical work of muscles. For better effect the devices are provided with an impedance generator allowing to control the individual physical work of each patient.

The trainer may have various building composition, different types of impedance generators and methods of their control /1, 2, 3, 4, 5, 6/.

Prior art teaches on use of a therapeutic effect of magnetic field for prophylaxis and treatment of various organs of a human body. The prior devices for magnetotherapy produce favorable effect both on the whole human body and on its selected organs /7, 8, 9/. In particular, devices for pulse magnetotherapy of gynecological diseases, prostatitis, etc., use pulse magnetic fields located in the immediate vicinity to treated organs /10, 11/. The devices are generally used at clinics and require constant control of medical personnel.

The claimed invention provides a device for dynamic physical work of the locomotor system of a human body. The seat of the device is mechanically connected to the dynamic elements for fisical work of musculs. The seat further comprises elements for carring out magnetotherapy of lumbar, coxofemoral and pelvic organs of a human body. The elements comprise a magnetic inductor, integral within the seat, and an impulse generator connected with the magnetic inductor through a modulating device.

The device additionally comprises a motion detector of the dynamic element. Physical work of a patient combined with the magnetic field effecting the body organs improves circulation of the blood, metabolism, hormonal processes, rehabilitation activity of physiological functions. A seats position of a patient rotating (pressing) the dynamic elements produces alternating compression and displacement of lumbar and coxofemoral organs of a human body making thereby massage of the organs. At the moment the motion detector generates a signal and supplies it to the modulating device. Accordingly, the effect of the magnetic field is synchronised with the location of an organ which is more favourable for creating an effect. Certain position of the locomotor system at maximum extension of muscular tissue provide the best approach of internal organs and the inductor, in particular of the postate and the inductor.

The device is additionally equipped with a audiosystem for listening-in music. Synchronously with the physical work on the trainer a patient is listening to harmonious musical sounds of the frequency that stimulates natural functions of a certain human organ. In parallel to that a signal from the audiosystem is supplied to the modulating device. Thereby the magnetic field is synchronized with the musical sound vibration effecting the human organ during listening-in.

The use of the aforementioned elements eliminates the necessity to introduce the inductor into the body and affords to use the magnetotherpy method and device outside a clinic.

A bicycle trainer serves an example of an embodiment of the invention.

FIG. 1 is a diagram of the basic principle for carrying out the invention regarding magnetotherapy of a prostate. The claimed device for prophylaxis and treatment of lumbar and coxofemoral organs of a human body comprises a supporting frame having a base 1, a seat 2, dynamic elements 6, magnetic inductor 3 located in the seat 2, pulse generator 7 connected with the inductor 3 through the modulating device 8.

Figure 2:
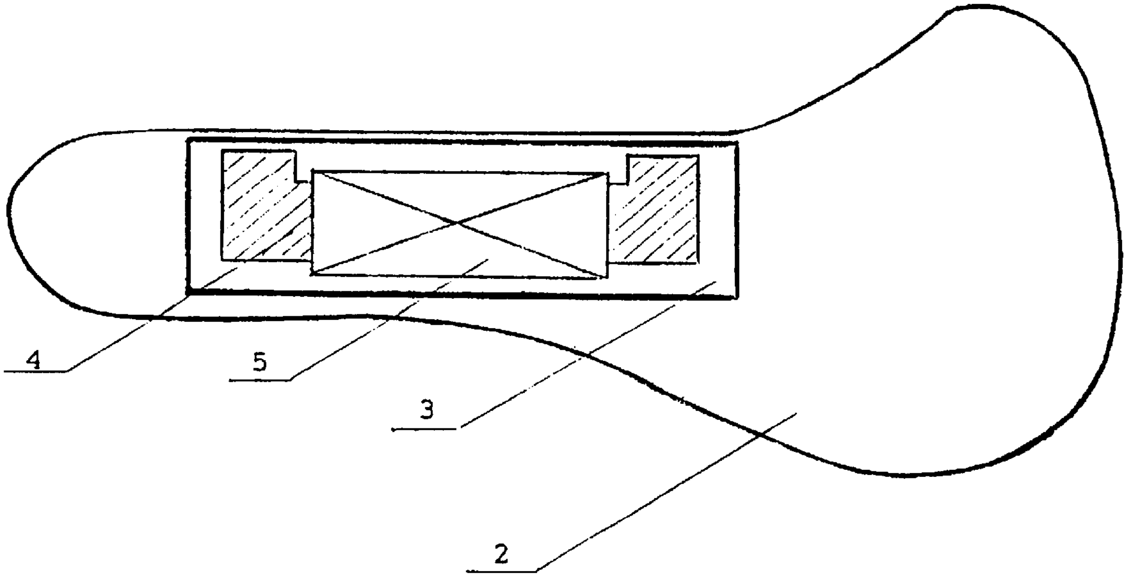

FIG. 2 is a general view of the seat 2 of the bicycle trainer. The seat 2 includes the inductor 3 located inside it and comprising a magnetic conductor 4 and an electric coil 5 producing a local magnetic field. Location of the inductor 3 in the seat 2 provides maximum approach of the inductor to the lumbar and coxofemoral organs of a human body.

The inductor 3 is pointed to provide maximum approach to the prostate and to locate and concentrate the magnetic field in the immediate vicinity to the prostate during the physical work.

A signal from the pulse generator 7 is supplied to the electric coil 5 of the inductor 3 through the modulating device 8 forming a magnetic field of specified characteristics. In one of the embodiments the inductor 3 may be a set of electromagnetic elements, then the modulating device 8 operates as a switching device as well.

The trainer is additionally provided with a detector of motion of a dynamic element 9 connected with the control input of the modulating device 8. The said embodiment of the claimed device allows to synchronise the magnetic field modulation with rotating (pressing) of dynamic elements registering thereby the point of the best approach of the organ with the inductor 3. During rotation of dynamic elements 6, points of magnetic field modulation are selected so that to agree them with the points of the maximum strain of the muscles of the lumbar and coxofemoral organs of a human body and with approach of the prostate to the inductor 3, intensifying thereby effectiveness of the prostate massage.

Exercises on trainers may be also accompanied by a stimulating sound effect. Prior art describes selective effect on functional organ activity of a tone quality of musical instruments /12/. Prior art also discloses sound vibration effect on certain organs /13/. Further development of the claimed system is modulation of a magnetic field with a sound (harmonic) signal by supplying it from the output of the audiosystem 10 to the modulating device 8. The said embodiment of the device allows use of musical therapy in combination with magnetic therapy. Concurrent effecting of a harmonic sound and a magnetic field modulation intensify favourable effect of the device in use.

Thus, the claimed device allows to control the therapeutic treatment of human organs at lower characterics of magnetic field and to stimulate natural organ functions producing thereby greater treating effect.

The claimed device fabricated on the basis of a bicycle trainer was tested in a clinic and showed good results in prophylaxis and treatment of prostatitis. The device may be used for prophylaxis and treatment of diseases of lumbar and coxofemoral organs of a human body in sanatoria, trainer halls, at home, during long term human stay in a bounded space (e.g. in submariners, spaceships) allowing to disengage medical staff.

What is claimed is:

1. A device for prophylaxis of diseases of lumbar, coxofemoral and pelvic organs of a human body comprising a seat (2) with an integral magnetic inductor (3), a pulse generator (7), characterised in that the device comprises at least one dynamic element (6) for physical work of muscles that is mechanically connected to the seat (2), and the integral magnetic inductor (3) is connected to the pulse generator (7) through a modulating device (8) having a control input.

2. A device according to claim 1, further comprising a detector of motion (9) of the dynamic element (6) connected with the control input of said modulating device (8).

3. A device according to claim 1, further comprising an audio system (10) for listening to music, the output of which is connected to said modulating device (8).

* * * * *

UNITED STATES PATENT AND TRADEMARK OFFICE

CERTIFICATE OF CORRECTION

PATENT NO. : 6,592,510 B1
DATED : July 15, 2003
INVENTOR(S) : Sergey Vladimirovich Pletnev It is certified that error appears in the above-identified patent and that said Letters Patent is hereby corrected as shown below:

Title page,
Item [75], correct the spelling of the name of inventor to:
-- Sergey Vladimirovich Pletnev --

Signed and Sealed this

Twenty-eighth Day of October, 2003

JAMES E. ROGAN
*Director of the United States Patent and Trademark Office*